United States Patent
Paetsch et al.

(10) Patent No.: US 10,881,349 B2
(45) Date of Patent: Jan. 5, 2021

(54) TEMPERATURE-MONITORING EARBUD DEVICE

(71) Applicant: Bose Corporation, Framingham, MA (US)

(72) Inventors: Christopher R. Paetsch, Cambridge, MA (US); John H. Wendell, Boston, MA (US); Harsh A. Mankodi, Brighton, MA (US)

(73) Assignee: BOSE CORPORATION, Framingham, MA (US)

( * ) Notice: Subject to any disclaimer, the term of this patent is extended or adjusted under 35 U.S.C. 154(b) by 656 days.

(21) Appl. No.: 15/229,964

(22) Filed: Aug. 5, 2016

(65) Prior Publication Data

US 2018/0035947 A1    Feb. 8, 2018

(51) Int. Cl.
| | |
|---|---|
| *A61B 5/00* | (2006.01) |
| *G01K 1/14* | (2006.01) |
| *G01K 13/00* | (2006.01) |
| *A61B 5/01* | (2006.01) |
| *A61F 11/08* | (2006.01) |

(Continued)

(52) U.S. Cl.
CPC .............. *A61B 5/6817* (2013.01); *A61B 5/01* (2013.01); *A61B 5/7221* (2013.01); *A61F 11/08* (2013.01); *G01K 1/14* (2013.01); *G01K 13/002* (2013.01); *A61B 2562/0276* (2013.01); *A61B 2562/164* (2013.01); *G01K 7/02* (2013.01); *G01K 7/16* (2013.01)

(58) Field of Classification Search
CPC .................................................... A61B 5/6817
See application file for complete search history.

(56) References Cited

U.S. PATENT DOCUMENTS

| | | |
|---|---|---|
| 5,062,432 A | 11/1991 | James et al. |
| 2002/0181540 A1 | 12/2002 | Gerlitz |
| 2006/0153272 A1 | 7/2006 | Chen et al. |

(Continued)

FOREIGN PATENT DOCUMENTS

| | | |
|---|---|---|
| EP | 3020327 A1 | 5/2016 |
| WO | 2016039795 A1 | 3/2016 |

OTHER PUBLICATIONS

International Search Report & Written Opinion in International Patent Application No. PCT/US17/41452, dated Sep. 20, 2017.

(Continued)

*Primary Examiner* — Daniel L Cerioni
*Assistant Examiner* — Yasmeen S Warsi
(74) *Attorney, Agent, or Firm* — Schmeiser, Olsen & Watts LLP; Timothy P. Collins

(57) ABSTRACT

A device for measuring a body temperature includes an earbud configured for insertion into at least a portion of an ear canal of a user to thereby create a substantially sealed ear canal. A temperature sensing element is fixed to the earbud at a location in which the temperature sensing element is thermally coupled to air in the sealed ear canal when the earbud is at least partially inserted into the ear canal. The temperature sensing element has a temperature-dependent electrical characteristic. The temperature sensing element is in electrical communication with a circuit that is configured to determine a temperature of the air in the sealed ear canal of the user in response to the temperature-dependent electrical characteristic.

9 Claims, 4 Drawing Sheets

(51) Int. Cl.
  *G01K 7/16* (2006.01)
  *G01K 7/02* (2006.01)

(56) References Cited

U.S. PATENT DOCUMENTS

| | | |
|---|---|---|
| 2007/0091980 A1 | 4/2007 | Tanaka |
| 2010/0315258 A1 | 12/2010 | Hiramatsu et al. |
| 2012/0063487 A1 | 3/2012 | Albrecht |
| 2012/0087391 A1 | 4/2012 | Chen |
| 2012/0150482 A1 | 6/2012 | Yildizyan et al. |
| 2012/0257649 A1 | 10/2012 | Tanaka |
| 2013/0218022 A1 | 8/2013 | Larsen et al. |
| 2013/0275076 A1* | 10/2013 | Yildizyan ............... A61B 5/01 |
| | | 702/131 |
| 2014/0146982 A1* | 5/2014 | Pelosi ................. H04R 1/1008 |
| | | 381/174 |
| 2016/0213354 A1 | 7/2016 | Levin et al. |

OTHER PUBLICATIONS

International Preliminary Report on Patentability in PCT/US2017/041452 dated Feb. 14, 2019; 9 pages.

\* cited by examiner

TEMPERATURE-MONITORING EARBUD DEVICE

BACKGROUND

This disclosure relates to a device and method for non-contact monitoring of a temperature of a user. The device may be in the form of an earbud that determines the temperature of the air in a sealed ear canal.

SUMMARY

In one aspect, a device for measuring a body temperature includes an earbud, a temperature sensing element, and a circuit in electrical communication with the temperature sensing element. The earbud is configured for insertion into at least a portion of an ear canal of a user to thereby create a substantially sealed ear canal. The temperature sensing element is fixed to the earbud at a location at which the temperature sensing element is thermally coupled to air in the sealed ear canal when the earbud is at least partially inserted into the ear canal. The temperature sensing element having a temperature-dependent electrical characteristic. The circuit is configured to determine a temperature of the air in the sealed ear canal of the user in response to the temperature-dependent electrical characteristic.

Examples may include one or more of the following features:

The earbud may include a rigid body and may further include an eartip attached to and extending from the rigid body. The eartip and/or earbud may be formed from a conformable material. The temperature sensing element may be thermally coupled to the air in the sealed ear canal through an opening in the eartip.

The device may include a microprocessor or digital signal processor. The temperature sensing element may be a thermocouple, RTD or thermistor.

The circuit may be configured to determine air temperature, to determine a rate of change of the determined air temperature, and/or to compare the rate of change of the determined air temperature to a threshold rate.

In accordance with another aspect, a method of determining a body temperature includes determining, from a temperature-dependent electrical characteristic of a temperature sensing element, a temperature of the air near the temperature sensing element. The method also includes determining that an earbud is at least partially inserted into an ear canal of a user so that a substantially sealed ear canal is created. The temperature sensing element is fixed to a surface of the earbud and is thermally coupled to air in the sealed ear canal. The method further includes waiting for a period of time for a temperature of the air in the sealed ear canal to achieve a substantially constant value and reporting the temperature of the air in the sealed ear canal as determined from the temperature-dependent electrical characteristic of the temperature sensing element.

Examples may include one or more of the following features:

The period of time for the temperature of the air in the sealed ear canal to achieve the substantially constant value may be predetermined.

The waiting for a period of time may include monitoring the temperature-dependent electrical characteristic of the temperature sensing element until a rate of change of the temperature-dependent characteristic is less than a predetermined threshold rate.

The determining that the earbud is at least partially inserted into the ear canal may include determining that a rate of increase in a temperature sensed by the temperature sensing element exceeds a threshold rate.

The determining that the earbud is at least partially inserted into the ear canal may include determining that the temperature sensed by the temperature sensing element exceeds a threshold temperature.

Reporting the temperature may include transmitting data representing the temperature value to a circuit in communication with the earbud and/or storing a time-series of temperature values in a data storage element.

In accordance with another aspect, an earbud for measuring a body temperature includes a rigid body, an eartip, a temperature sensing element and a circuit. The eartip is attached to and extends from the rigid body. The eartip is formed of a conformable material. The rigid body and eartip are configured for insertion into at least a portion of an ear canal of a user to thereby create a substantially sealed ear canal. The temperature sensing element is fixed to the rigid body at a location in which the temperature sensing element is thermally coupled, through an opening in the compliant eartip, to air in the sealed ear canal when the eartip is at least partially inserted into the ear canal. The temperature sensing element has a temperature-dependent electrical characteristic. The circuit is in electrical communication with the temperature sensing element and is configured to determine a temperature of the air in the sealed ear canal of the user in response to the temperature-dependent electrical characteristic.

Examples may include one or more of the following features:

The rigid body may be formed from a thermoplastic material. The eartip may be formed of silicone rubber, nitrile rubber and polyurethane.

The earbud may further include a thermally conductive protective component disposed on the temperature sensing element.

BRIEF DESCRIPTION OF THE DRAWINGS

The above and further advantages of examples of the present inventive concepts may be better understood by referring to the following description in conjunction with the accompanying drawings, in which like numerals indicate like structural elements and features in various figures. The drawings are not necessarily to scale, emphasis instead being placed upon illustrating the principles of features and implementations.

DETAILED DESCRIPTION

Vital signs indicative of the state of body functions include pulse rate, temperature, respiration rate and blood pressure. In particular, body temperature can be monitored to provide insight to general physical health, fertility and sleep. One option is to measure the temperature of the skin; however, skin temperature can fluctuate with environmental conditions. Conventional body locations used to determine temperature include the mouth, armpit and rectum. These locations are too intrusive for long-term monitoring and may require that the measurement device be sterilized before use. Moreover, a sensor can cause discomfort to a user as the sensor may have one or more rigid components in contact with the user.

Examples of a non-contact device for measuring a body temperature, described below, avoid the problems described above. The device may be implemented in an earbud that a user may have for other purposes. For example, the earbud may be part of an audio playback or communications system, or may be used for noise reduction. At least a portion of the earbud may be formed of a conformable material that seals the ear canal of the user and provides comfort to the user across a range of activities, including strenuous exercise such as running and cycling. The conformable material helps to keep the earbud in place during strenuous activities. Alternatively, the earbud may be worn during periods of inactivity, including sleep. For example, the earbud may be worn by a user each night for a period of weeks or months to monitor body temperature for the purpose of determining sleep quality, to identify periods of fertility or to characterize the general health of the user.

Figure 1A:
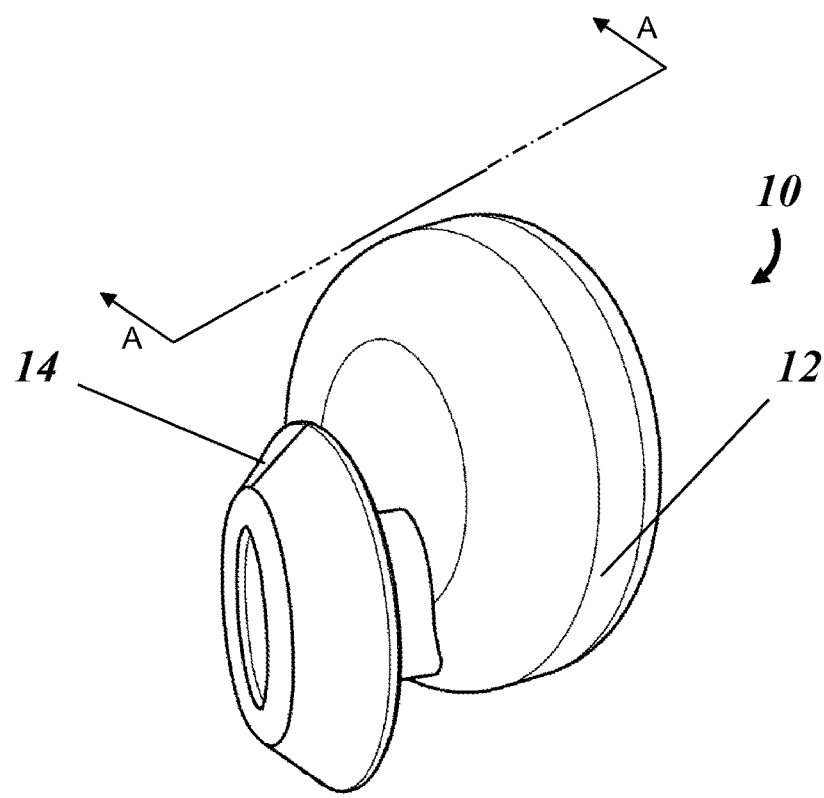
FIG. 1A and FIG. 1B are perspective and cross-sectional views, respectively, of an example of a device for measuring a body temperature.
Figure 1B:
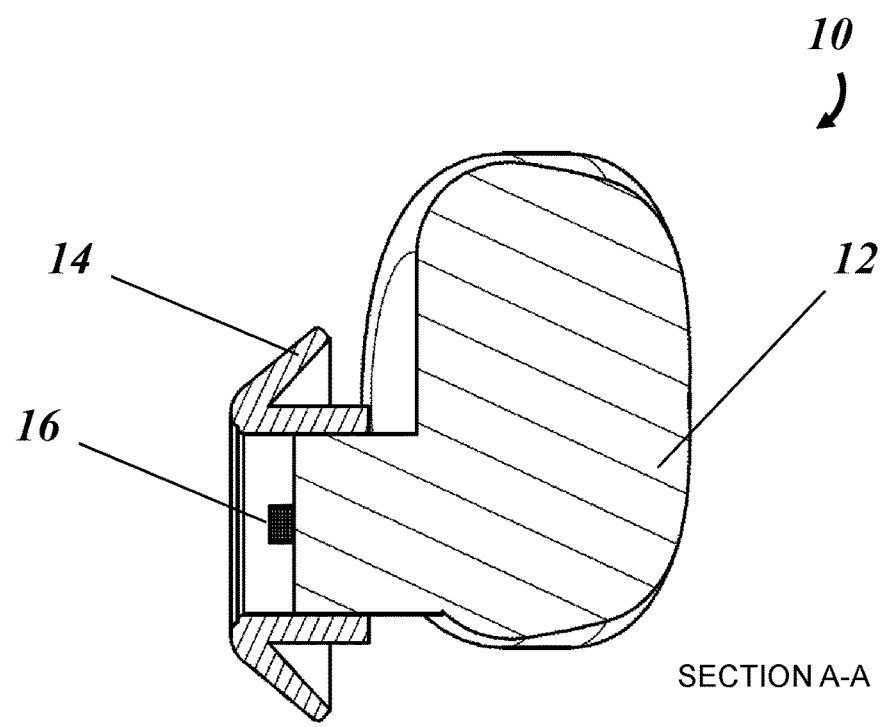

Referring to the perspective and cross-sectional views of FIG. 1A and FIG. 1B, respectively, an example of a device 10 for measuring a body temperature includes an earbud 12. The earbud 12 is configured for insertion into at least a portion of the ear canal of the user. The earbud 12 may include a rigid body, which may be made of a thermoplastic, such as nylon, polypropylene, acrylonitrile butadiene styrene (ABS) or polycarbonate, or other material. The earbud 12 is shown as having an attached eartip 14 extending from the rigid body and made from a conformable, biocompatible and low thermal conductivity material such as silicone rubber, nitrile rubber or polyurethane.

Figure 2:
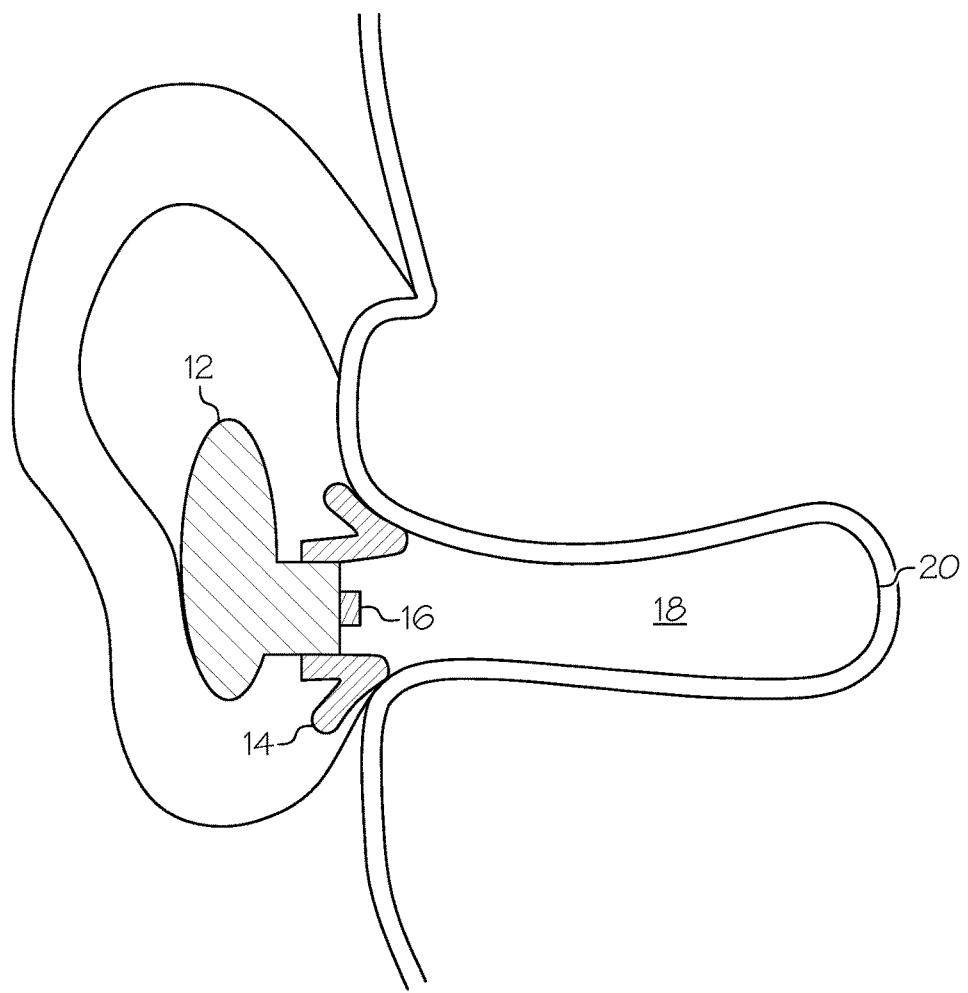
FIG. 2 is a cross-sectional illustration of the device of FIGS. 1A and 1B when inserted into an ear canal of a user.

The device 10 also includes a temperature sensing element 16 that is fixed to the earbud 12 at a location that allows the temperature sensing element 16 to be thermally coupled to air in the user's sealed ear canal 18, as shown in FIG. 2. The sealed ear canal 18 is defined as the cavity formed by the ear canal which terminates at one end at the eardrum 20 and at the opposite end at the earbud 12, where the earbud 12 sufficiently thermally isolates the cavity from the external environment. The seal created by the eartip 14 may not be a complete seal as long as any leakage is insufficient to significantly affect the temperature of the air trapped inside the sealed ear canal 18. In the example of FIG. 2, the sealed ear canal 18 is shown significantly shorter than is typical, for clarity. In one example, the temperature sensing element 16 is mounted to a printed circuit board located within the earbud 12. Thermal coupling can be direct coupling to the air in the sealed ear canal 18, that is, the temperature sensing element 16 may be directly exposed to the air in the sealed ear canal 18 through an opening in the eartip 14. Alternatively, a thermally conductive component may be disposed on the temperature sensing element 16 and may protect the sensing element from damage. Preferably, the thermally conductive component may conduct heat to the temperature sensing element 16 with insignificant thermal loss using a conformable material such as silicone with thermally conductive additives like carbon black or alumina. A fine metal screen may also be used to protect the temperature sensing element 16.

The temperature sensing element 16 has a temperature-dependent electrical characteristic. By way of a specific example, the temperature sensing element 16 may be a thermocouple which generates a temperature-dependent voltage according to the thermoelectric effect. The voltage can be measured and converted to a corresponding temperature. Thermocouples are an inexpensive type of temperature sensor and typically do not require power to operate, although circuitry used to process the voltage signal generally requires a battery or other electrical power source. One specific example of a thermocouple that may be used is a "type T" fine gage bare wire thermocouple having a 0.001 in. (25 μm) diameter and available from Omega Engineering, Inc.

In an alternative example, the temperature sensing element 16 may be a thermistor or resistance temperature detector (RTD), devices which have a temperature-dependent resistance. Thermistors and RTD sensors are similar in that both are passive sensors; however thermistors typically have a resistance which decreases with increasing temperature and RTDs have a resistance which increases with increasing temperature. A determination of the value of the resistance of the thermistor or RTD may be made based on a measurement of a voltage across, or a current flowing through, the temperature-dependent resistance element as is known in the art. The Honeywell 702 Series (2.3 mm×1.4 mm×0.52 mm) temperature sensor and the Honeywell 175 Series (3.2 mm×1.6 mm×1.2 mm) temperature sensor are examples of a suitable RTD and thermistor, respectively.

The type of temperature sensing element 16 can be selected according to the intended use of the device. For example, the accuracy of some thermocouples is approximately 1.0° C. and the accuracy of some thermistors is a few tenths of a degree Celsius or less. Thus the type of temperature sensing element used can be based on the purpose for the temperature measurement. For example, a 1.0° C. accuracy thermocouple may be sufficient for sleep cycle monitoring.

The device 10 also includes a circuit that is in electrical communication with the temperature sensing element 16. The circuit may be provided on a printed circuit board within the earbud 12 and may include a power source (e.g., battery). Alternatively, part or all of the circuit may be remote to the earbud, and may be in electrical communication with the temperature sensing element 16 and/or other device components in the earbud 12 through a flexible cable or a wireless link (e.g. Wi-Fi, Bluetooth® or other wireless link). The circuit may include circuit components used to sense a voltage across the sensing element 16 or a current through the sensing element 16, one or more analog-to-digital converters (ADCs) and/or at least one processing module such as a microprocessor or digital signal processor (DSP). In some examples, the circuit may include local storage for storing data associated with temperatures sensed at different times. For example, the data may include the sensed temperature of the air in the sealed ear canal 18 determined according to a fixed sampling rate. In some instances the circuit may include a commercially-available integrated circuit (IC) that combines one or more of signal conditioning, ADC, control logic, digital signal processing (DSP), power management and a communication interface, ultimately providing as output a digital signal indicative of temperature. The circuit may also be configured to transmit data to an external device. For example, the device 10 may transmit temperature data through a cable or wireless link to a smartphone, a desktop or laptop personal computer (PC), or the like where the data can be analyzed and presented to a device user or other analyst. Alternatively, the data may be further transmitted over a network to a remote computing device for storage and/or analysis.

Figure 3:
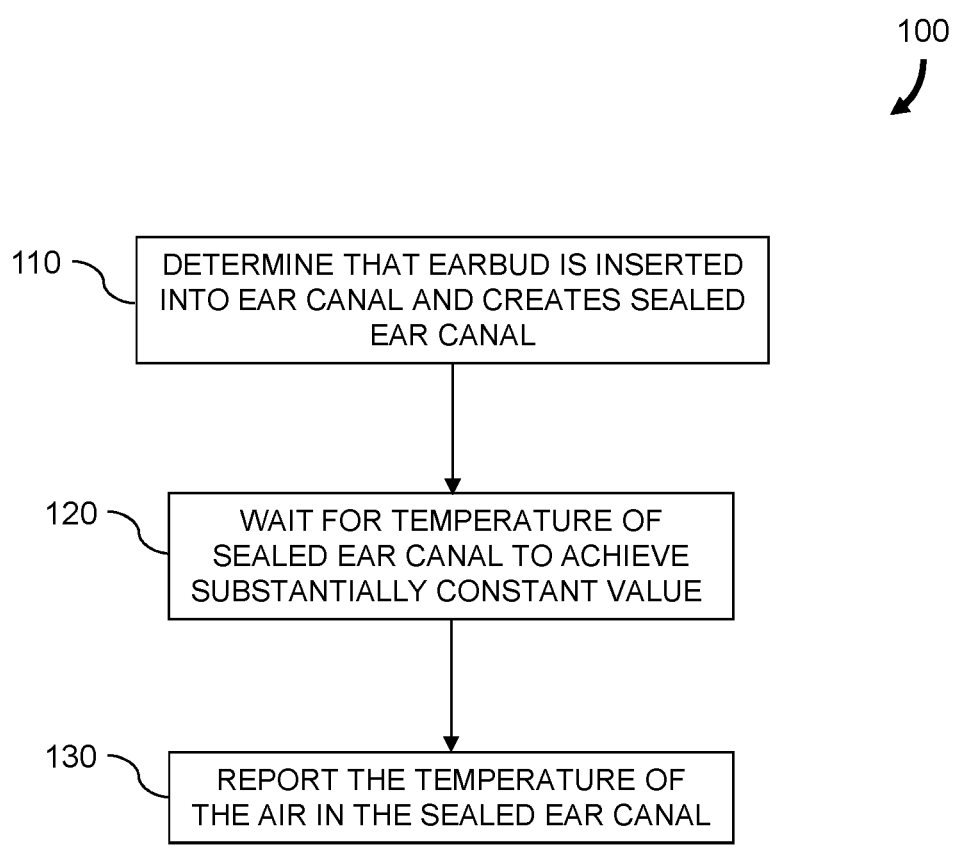
FIG. 3 is a flowchart representation of an example of a method of determining a body temperature.

FIG. 3 is a flowchart representation of an example of a method 100 of determining a body temperature. A user inserts an earbud at least partially into the user's ear canal so that the ear canal and earbud create a sealed ear canal. The portion of the earbud that is in contact with the outer end of the ear canal is preferably formed from a conformable material to improve the sealing of the ear canal and may instead be an attachable and removable eartip. The earbud includes a non-contact temperature sensing element, as described above, which is fixed to a surface of the earbud so that the sensing element is thermally coupled to air within the sealed ear canal.

According to the method 100, a determination (110) is made that the earbud is inserted into the ear canal. This determination can be made by sensing that a rate of increase in a temperature sensed by the temperature sensing element is greater than a threshold rate. Alternatively, the determination can be made by discerning that the temperature sensed by the temperature sensing element is greater than a predefined temperature. For example, the predefined temperature can be a temperature that is above a typical ambient temperature and below a lower end of an expected range of body temperatures. As an unsealed ear canal may have a temperature between ambient temperature and the body temperature, the predefined temperature is preferably established closer to body temperature, for example, the predefined temperature may be 32° C. Thus determining that the sensed temperature has transitioned from less than the predefined temperature to greater than the predefined temperature indicates that the user has recently inserted the earbud into the ear canal. Conversely, determining that the temperature sensed by the temperature sensing element has transitioned from greater than the predefined temperature to less than the predefined temperature indicates that the user has removed the earbud from the ear canal. In one example, a determination that the user has removed the earbud may be used to reduce a power supplied to the device and/or an auxiliary device (e.g., an audio source device) to conserve power or preserve battery life.

Figure 4:
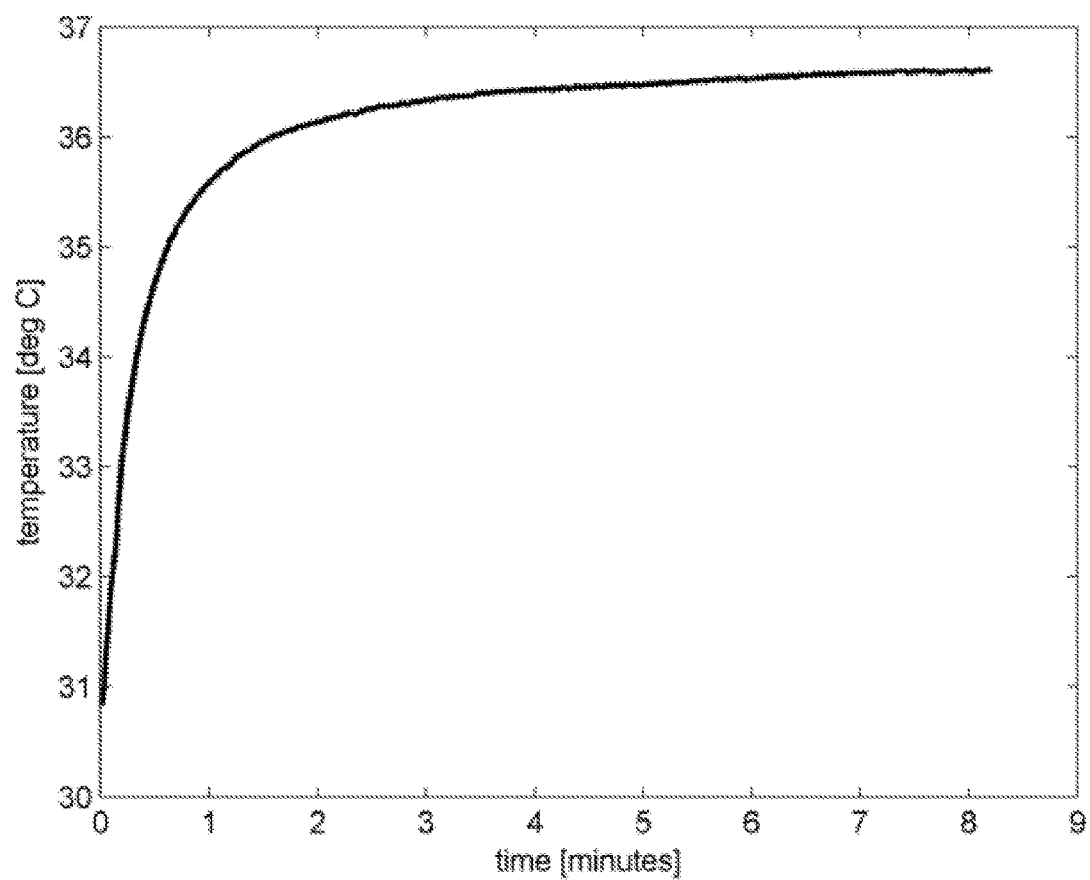
FIG. 4 is a graphical representation of the air temperature inside a sealed ear canal of a user as a function of time.

If a determination is made (110) that the earbud is at least partially inserted into the ear canal, the method 100 continues by waiting (120) for a period of time for the temperature of the seal ear canal to achieve a substantially constant value. As used herein, a substantially constant value means a temperature value that corresponds to the warming of the air in the ear canal beyond which little or no further warming is expected by waiting for additional time unless there is a true body temperature change. Referring also to FIG. 4, an example of the air temperature inside a sealed ear canal of a user is shown as a function of time. The air temperature of the sealed ear canal is seen to increase rapidly, on the order of 4° C./minute, during the first minute after the ear canal is first sealed (at time 0 minutes). After additional time, the rate of temperature increase slows until after approximately five minutes the temperature of the air in the sealed ear canal is within a few tenths of a degree Celsius of its equilibrium value. It should be noted that the equilibrium value of approximately 36.5° C. is less than a typical user core body temperature of approximately 37° C. In one example, the waiting period is predetermined to be a specific value (e.g., five minutes). In an alternative example, the period of time is not predetermined and instead is based on a sensing that the temperature of the sealed ear canal is nearly or fully stabilized. For example, the period of time may be based on sensing that a rate of increase in a temperature sensed by the temperature sensing element has decreased to less than a threshold rate (e.g., 0.3° C./minute).

Once the temperature of the air in the sealed ear canal is substantially constant, the measured temperature is reported 130 (transmitted or logged) as mentioned above. Generally the determined temperature is representative of the body temperature of the user although it will be recognized, as with conventional body thermometers and similar devices, that the determined body temperature may be different from that sensed at other locations of the human body using various temperature sensing techniques. Advantageously, variations in the external (ambient) temperature have substantially no effect on the air temperature inside the sealed ear canal.

In the examples above, the devices are described only with respect to their audio and temperature measurement capability; however, it should be recognized that one or more additional sensors may be included with the earbud. By way of specific examples, the earbud may also be provided with a sensor to measure a pulse rate of the user or a microphone to detect sound pressure in the canal.

A number of implementations have been described. Nevertheless, it will be understood that the foregoing description is intended to illustrate, and not to limit, the scope of the inventive concepts which are defined by the scope of the claims. Other examples are within the scope of the following claims.

What is claimed is:

1. A method of determining a body temperature, the method comprising:
   determining, from a temperature-dependent electrical characteristic of a non-contact temperature sensor, a temperature of the air near the temperature sensing element;
   determining solely from temperature data acquired from the non-contact temperature sensor that an earbud is at least partially inserted into an ear canal of a user so that a sealed ear canal is created, the non-contact temperature sensor being fixed to a surface of the earbud and being thermally coupled to air in the sealed ear canal;
   waiting for a period of time for a temperature of the air in the sealed ear canal to achieve a substantially constant value; and
   reporting the temperature of the air in the sealed ear canal as determined from the temperature-dependent electrical characteristic of the non-contact temperature sensor.

2. The method of claim 1 wherein the period of time for the temperature of the air in the sealed ear canal to achieve the substantially constant value is predetermined.

3. The method of claim 1 wherein the waiting for a period of time comprises monitoring the temperature-dependent electrical characteristic of the non-contact temperature sensor until a rate of change of the temperature-dependent characteristic is less than a predetermined threshold rate.

4. The method of claim 1 wherein determining that the earbud is at least partially inserted into the ear canal comprises determining that a rate of increase in a temperature sensed by the non-contact temperature sensor exceeds a threshold rate.

5. The method of claim 1 wherein determining that the earbud is at least partially inserted into the ear canal comprises determining that the temperature sensed by the non-contact temperature sensor exceeds a predefined temperature.

6. The method of claim 1 wherein reporting the temperature comprises storing a time-series of temperature values in a data storage element.

7. The method of claim 1 wherein reporting the temperature comprises transmitting data representing the temperature value to a circuit in communication with the earbud.

8. The method of claim 7 wherein power to a device in communication with the earbud is reduced in response to the data transmitted to the circuit.

9. The method of claim 8 wherein the device in communication with the earbud is an audio source device.

* * * * *